United States Patent [19]
Jacewicz et al.

[11] Patent Number: 6,093,828
[45] Date of Patent: Jul. 25, 2000

[54] FORM OF (E)-3-[6-[[(2,6-DICHLOROPHENYL)-THIO]METHYL]-3-(2-PHENYLETHOXY)-2-PYRIDINYL]-2-PROPENOIC ACID

[75] Inventors: Victor Witold Jacewicz, Tunbridge Wells; Michael Anthony Harris, Bletchingley; Richard Keith Anderson, East Grinstead, all of United Kingdom

[73] Assignee: SmithKline Beecham p.l.c., Brentford, United Kingdom

[21] Appl. No.: 08/945,372

[22] PCT Filed: Apr. 2, 1996

[86] PCT No.: PCT/EP96/01466

§ 371 Date: Dec. 16, 1997

§ 102(e) Date: Dec. 16, 1997

[87] PCT Pub. No.: WO96/33174

PCT Pub. Date: Oct. 24, 1996

[30] Foreign Application Priority Data

Apr. 21, 1995 [GB] United Kingdom .................... 9508137

[51] Int. Cl.[7] .......................... C07D 211/72; C07D 211/84; C07D 213/62; A61K 31/44
[52] U.S. Cl. ............................................. 546/294; 514/347
[58] Field of Search ................................ 546/294; 514/347

[56] References Cited

FOREIGN PATENT DOCUMENTS

| WO93/06085 | 4/1993 | WIPO . |
| WO94/00433 | 1/1994 | WIPO . |
| WO94/00437 | 1/1994 | WIPO . |
| WO95/00487 | 1/1995 | WIPO . |

*Primary Examiner*—Minna Moezie
*Attorney, Agent, or Firm*—James M. Kanagy; Charles M. Kinzig

[57] ABSTRACT

A novel physical form of (E)-3-[6-[[(2,6-dichlorophenyl)-thio]methyl]-3-(2-phenylethoxy)-2-pyridinyl]-2-propenoic acid and its use in therapy is disclosed.

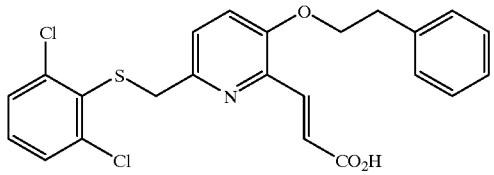

3 Claims, No Drawings

FORM OF (E)-3-[6-[[(2,6-DICHLOROPHENYL)-THIO]METHYL]-3-(2-PHENYLETHOXY)-2-PYRIDINYL]-2-PROPENOIC ACID

This application is a 371 of PCT/EP96/01466 filed Apr. 2, 1996.

The present invention relates to a novel physical form of the (E)-3-[6-[[(2,6-dichlorophenyl)-thio]methyl]-3-(2-phenylethoxy)-2-pyridinyl]-2-propenoic acid, pharmaceutical compositions containing it and its use in therapy.

(E)-3-[6-[[(2,6-dichlorophenyl)-thio]methyl]-3-(2-phenylethoxy)-2-pyridinyl]-2-propenoic acid, that is to say, the compound of the following structure:

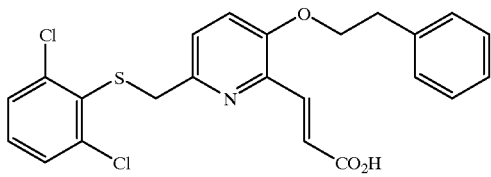

is known in the art as a compound which is useful as a leukotriene antagonist. In particular, the compound is disclosed in WO94/00437 as being useful for the treatment of psoriasis. Patients suffering from psoriasis are often exposed to sunlight as part of their therapy, and such exposure can potentially cause degradation of pharmaceutically active compounds. There is therefore a need for topical formulations containing this compound which are resistant to exposure to sunlight.

(E)-3-[6-[[(2,6-dichlorophenyl)-thio]methyl]-3-(2-phenylethoxy)-2-pyridinyl]-2-propenoic acid can exist in a number of different physical forms (also known as polymorphs).

The present invention therefore provides, in a first aspect (E)-3-[6-[[(2,6-dichlorophenyl)-thio]methyl]-3-(2-phenylethoxy)-2-pyridinyl]-2-propenoic acid in the form identified by the following characteristics:
infra-red absorption bands at about 697, 743 and 884 cm$^{-1}$.
a single melting endotherm with onset at about 140° C. (minimum at 142.2° C.) as identified by differential scanning calorimetry.
x-ray diffraction scattering (Cu source) at 9.2, 16.4, 23.3, 26.8 & 27.3 degrees Hereinafter the form having these characteristics will be referred to as (E)-3-[6-[[(2,6-dichlorophenyl)-thio]methyl]-3-(2-phenylethoxy)-2-pyridinyl]-2-propenoic acid Form II.

For the avoidance of doubt, the above infra-red absorption bands above are those obtained from a nujol mull.

(E)-3-[6-[[(2,6-dichlorophenyl)-thio]methyl]-3-(2-phenylethoxy)-2-pyridinyl]-2-propenoic acid in the polymorphic form disclosed in WO 94/00437 has the following physical characteristics:
infra-red absorption bands at about 704, 758 and 896 cm$^{-1}$.
a small endotherm followed by a small exotherm from 118° C. to 138° C. and a melting endotherm with onset at about 140° C. as identified by differential scanning calorimetry.
x-ray diffraction scattering (Cu source) at 10.1, 20.0, 23.0, 24.0 and 25.4 degrees.

The polymorphic form having the above characteristics is designated as Form I.

(E)-3-[6-[[(2,6-dichlorophenyl)-thio]methyl]-3-(2-phenylethoxy)-2-pyridinyl]-2-propenoic acid Form II has certain surprising advantages when compared with the previously identified physical forms. For example (E)-3-[6-[[(2,6-dichlorophenyl)-thio]methyl] -3-(2-phenylethoxy)-2-pyridinyl]-2-propenoic acid Form II exhibits much greater stability to light compared with the Form I polymorph.

The invention also provides in a further aspect (E)-3-[6-[[(2,6-dichlorophenyl)-thio]methyl]-3-(2-phenylethoxy)-2-pyridinyl]-2-propenoic acid Form II for use in therapy, in particular in the treatment of psoriasis. When used in therapy, (E)-3-[6-[[(2,6-dichlorophenyl)-thio]methyl]-3-(2-phenylethoxy)-2-pyridinyl]-2-propenoic acid Form II can be formulated in a standard pharmaceutical composition using techniques well known in the art of pharmacy.

In further aspect, the present invention provides a pharmaceutical composition comprising (E)-3-[6-[[(2,6-dichlorophenyl)-thio]methyl]-3-(2-phenylethoxy)-2-pyridinyl]-2-propenoic acid Form II in association with a pharmaceutical carrier.

It will be apparent to those skilled in the art that a pharmaceutical composition comprising (E)-3-[6-[[(2,6-dichlorophenyl)-thio]methyl]-3-(2-phenylethoxy)-2-pyridinyl]-2-propenoic acid Form II in substantially pure form will exhibit the above advantages. By 'substantially pure form' is meant at least 50% pure, preferably 80–90% pure, and most preferably greater than 95% pure.

Compositions comprising mixtures of Form I and Form II polymorphs form a further aspect of the invention.

In a further aspect, the present invention provides the use of (E)-3-[6-[[(2,6-dichlorophenyl)-thio]methyl]-3-(2-phenylethoxy)-2-pyridinyl]-2-propenoic acid Form II in the manufacture of a medicament for the treatment of psoriasis. The invention also provides a method of treatment of psoriasis which comprises administration to a host in need thereof an effective amount of (E)-3-[6-[[(2,6-dichlorophenyl)-thio]methyl]-3-(2-phenylethoxy)-2-pyridinyl]-2-propenoic acid Form II.

The dosage range for the compound of the present invention is expected to be in the range of from about 5 to about 1000 mg daily, preferably about 10 to about 200 mg daily. For topical use for the treatment of psoriasis the dosage range will depend on the size of the affected area and the severity of the disease.

When administered in accordance with the invention, no unacceptable toxicological effects are expected with the compounds of the invention.

The following examples illustrate the invention.

EXAMPLE 1

A foil covered 50 mL conical flask was charged with crude (E)-3-[6-[[(2,6-dichlorophenyl)-thio]methyl]-3-(2-phenylethoxy)-2-pyridinyl]-2-propenoic acid (prepared according to the method disclosed in WO/95/00487) (5.0 g) and propan-2-ol (25 mL). The suspension was heated to reflux and the resultant solution filtered through paper under reduced pressure into a foil-covered vial containing a magnetic follower. The vial was sealed and the filtrate stirred for 3 hours allowing to cool to ambient temperature. The white solid was filtered, drained well, top washed with diethyl ether (3 mL) (see note) and dried under vacuum to give (E)-3-[6-[[(2,6-dichlorophenyl)-thio]methyl]-3-(2-phenylethoxy)-2-pyridinyl]-2-propenoic acid as a snow-white solid (4.36 g, 88% recovery).

Note: Diethyl ether was used to aid the vacuum drying, it may be omitted or replaced by a wash with cold propan-2-ol without affecting the yield.

The product had the following characteristics:
infra-red absorption bands at about 697, 743 and 884 cm$^{-1}$.
a single melting endotherm with onset at about 140° C. (minimum at 142.2° C.) as identified by differential scanning calorimetry.

x-ray diffraction scattering (Cu source) at 9.2, 16.4, 23.3, 26.8 and 27.3 degrees.

EXAMPLE 2

Comparison of light stability of crystalline forms.

Samples of form I and form II were exposed to xenon light (85,000 lux) in a Heraeus Sun Test CPS light cabinet for 4 hours. The samples were analysed before and after exposure to light by HPLC for relative response and impurity profile.

| Sample | Relative response to unexposed | Area % of main peak | Area % of Dimer |
| --- | --- | --- | --- |
| Form I unexposed | 100% | 99.5% | 0.1% |
| Form I exposed | 0.7% | 1.1% | 75.8% |
| Form II unexposed | 100% | 97.7% | nd |
| Form II exposed | 96.5% | 98.1% | <0.1% | nd = not detected.

The dimer refers to a cyclobutane dimer of (E)-3-[6-[[(2,6-dichlorophenyl)-thio]methyl]-3-(2-phenylethoxy)-2-pyridinyl]-2-propenoic acid, which is the principle degradation product of the form I compound. The results clearly show that the form II is considerably more stable than form I on exposure to xenon light. After 4 hours exposure form I degrades almost completely.

What is claimed is:

1. The polymorph of the compound (E)-3-[6-[[(2,6-dichlorophenyl)-thio]methyl]-3-(2-phenylethoxy)-2-pyridinyl]-2-propenoic acid in the form having the following characteristics:

(a) infra-red absorption bands at about 697, 743 and 884 $cm^{-1}$, (b) a single melting endotherm which has a minimum onset at about 142.2° C. as identified by differential scanning calorimetry, and (c) x-ray diffraction scattering Cu source, having peaks at 9.2, 16.4, 23.3, 26.8 and 27.3 degrees.

2. A pharmaceutical composition comprising the form of (E)-3-[6-[[(2,6-dichlorophenyl)-thio]methyl]-3-(2-phenylethoxy)-2-pyridinyl]-2-propenoic acid as described in claim 1 in association with a pharmaceutically acceptable carrier.

3. A pharmaceutical composition comprising a pharmaceutically acceptable excipient, the polymorph of claim 1, and the polymorph of (E)-3-[6-[[(2,6-dichloro-phenyl)-thio]methyl]-3-(2-phenylethoxy)-2-pyridinyl]-2-propenoic acid having the characteristics:

(a) infra-red absorption bands at about 704, 758 and 896 $cm^{-1}$, (b) a endotherm followed by a exotherm from 118° C. to 138° C. and a melting endotherm with onset at about 140° C. as identified by differential scanning calorimetry, and (c) x-ray diffraction scattering, Cu source, having peaks at 10.1, 20.0, 23.0, 24.0 and 25.4 degrees.

* * * * *